US005556778A

United States Patent [19]

Sacchettini

[11] Patent Number: 5,556,778
[45] Date of Patent: Sep. 17, 1996

[54] CRYSTALLINE INHA ENZYME-NADH COMPLEX

[75] Inventor: James Sacchettini, New Rochelle, N.Y.

[73] Assignee: Albert Einstein College of Medicine of Yeshiva University, A Division of Yeshiva University, Bronx, N.Y.

[21] Appl. No.: 491,146

[22] Filed: Jun. 16, 1995

Related U.S. Application Data

[63] Continuation of Ser. No. 307,376, Sep. 16, 1994, abandoned, which is a continuation-in-part of Ser. No. 234,011, Apr. 28, 1994.

[51] Int. Cl.[6] .............................. C12N 9/02; C30B 29/58
[52] U.S. Cl. ............................................. 435/189; 117/927
[58] Field of Search .............................. 435/189; 117/927

[56] References Cited

PUBLICATIONS

Dessen et al. (1995) Science, 267, "Crystal Structure and Function of the Isoniazid Target of Mycobacterium tuberculosis", pp. 1638–1641.
King (10 Apr. 1989) Chem. Eng. News, pp. 32–54.
Banerjee et al. (1994) Science, 263, 227–230.

Primary Examiner—David M. Naff
Assistant Examiner—Jon P. Weber
Attorney, Agent, or Firm—Amster, Rothstein & Ebenstein

[57] ABSTRACT

The crystallized complex of NADH and Inha enzyme from Mycobacterium tuberculosis is presented. Methods of designing inhibitors to the Inha enzyme and subsequent treatment with those inhibitors of infection by M. tuberculosis are disclosed.

1 Claim, 1 Drawing Sheet

CRYSTALLINE INHA ENZYME-NADH COMPLEX

STATEMENT OF GOVERNMENT INTEREST

This invention was made with government support under NIH Grant Numbers AI33696 and AI27160. As such, the government has certain rights in the invention.

CROSS REFERENCE TO RELATED APPLICATION

This Application is a continuation of U.S. Application No. 08/307,376, filed Sep. 16, 1994, now abandoned which is a Continuation-In-Part of U.S. application Ser. No. 08/234,011 filed Apr. 28, 1994, currently pending.

FIELD OF THE INVENTION

This invention is directed to InhA enzyme crystals, to the use of said InhA enzyme crystals to determine the three dimensional structure of InhA enzyme and to the three dimensional structure of said InhA enzyme. The three dimensional structure of the InhA enzyme allows for the development of compounds which inhibit the biochemical activity of InhA enzyme in bacteria. Said compounds are developed and administered to treat bacterial infection.

BACKGROUND OF THE INVENTION

Tuberculosis remains the largest cause of death in the world from a single infectious disease and is responsible for one in four avoidable adult deaths in developing countries. Infection with drug-sensitive strains of *Mycobactrium tuberculosis* can be effectively cured with a combination of isoniazid, ethionamide, rifampicin and pyrazinamide. However, the emergence of multiple drug resistant strains of *M. tuberculosis* has resulted in fatal outbreaks in the United States.

Isoniazid was first reported to be active against *M. tuberculosis* in 1952, when it was shown to have a highly specific activity against *M. tuberculosis* and *M. bovis*, with less but considerable activity against other mycobacteria. Although isoniazid is one of the most widely used anti-tuberculosis drugs for both therapy and prophylaxis, its precise target of action on *Mycobactrium tuberculosis* has remained unknown. Isoniazid was first synthesized as an organic compound in 1912, but it was not until 1952 that three independent groups discovered that it had anti-tuberculosis activity. The discovery that ethionamide had anti-tuberculosis activity was predicated on the discovery that nicotinamide showed some tuberculostatic activity against *M. tuberculosis*.

Resistance to isoniazid was first reported in 1953, but in recent years has been as high as 26% in some areas of the United States. A fraction of isoniazid-resistant strains had been shown to be associated with a loss of catalase activity (see Lefford et al., *Tubercle*, Vol. 47, p. 109 (1966) and Stoecle et al., *J. Inf. Dis.*, Vol. 168, p. 1063 (1993)). The catalase gene (katG) was recently cloned and deletions of this gene were shown to be correlated with isoniazid resistance in certain *M. tuberculosis* isolates (see Zhang et al., *Nature*, Vol. 358, pp. 591–593 (1992)). Furthermore, transfer of the *M. tuberculosis* katG gene to isoniazid-resistant *M. smegmatis* strains results in the acquisition of isoniazid-sensitivity, suggesting that the presence of the catalase activity results in the sensitivity of *M. tuberculosis* to isoniazid (see Middlebrook, *Am. Rev. Tuberc.*, Vol. 65, pp. 765–767 and Zhang et al., *Molec. Microbiol.*, Vol. 8, pp. 521–529 (1993)).

Although catalase may be important to the action of isoniazid, it does not appear to be the target of action of the drug. Isoniazid-resistance can be accounted for by the loss of catalase activity; however, only 25% of isoniazid-resistant isolates appear to be catalase-negative. Previous studies have shown that low-level isoniazid resistance correlated not with the loss of catalase activity, but rather with the co-acquisition of ethionamide resistance (see Canetti, *Am. Rev. Respir. Dis.*, Vol. 92, p. 687 (1965); Grumbach, *Rev. Tuber.*, Vol. 25, p. 1365 (1961); Lefford, *Tubercle*, Vol. 47, p. 198 (1966) and Hok, *Am. Rev. Respir. Rev.*, Vol. 90, pp. 468–469 (1964)).

Drug resistance can often be mediated by the accumulation of mutations in the gene encoding the targets that result in reduced binding of drugs to their targets. For example, rifampicin resistance is often mediated by mutations in the gene encoding the β' subunit of RNA polymerase. Alternatively, trimethoprim resistance can be mediated by mutations causing amplification in a target dihydrofolate reductase.

Without the availability of genetic systems for the mycobacteria, the identification of the precise target of action of isoniazid and ethionamide could not be determined. Hence, it has been desirable to identify the specific point mutations that confer resistance to isoniazid and ethionamide in *M. tuberculosis*. The enzyme which is the target of action of isoniazid has been identified and denoted as InhA, and the gene which encodes the enzyme InhA has been denoted inhA (see Banerjee et al., *Science*, Vol. 263, pp. 227,230 (January 1994)). As used herein, "InhA" includes InhA enzyme and any mutants thereof.

The inhA gene shares significant homology with a gene which codes for the EnvM protein from *E. coli* and *Salmonella typhimurium*, which is known to be involved in fatty acid (lipid or mycolic acid) biosynthesis. The enzyme InhA, encoded by the inhA gene, is necessary for mycolic acid biosynthesis.

Mycolic acids, also referred to herein as lipids, are long chain fatty acids (60 to 80 carbons in lengths) that are major constituents of a mycobacterial cell wall. They are thought to be the chemical moieties responsible for the characteristic acid-fastness of mycobacteria and form the waxy layer of mycobacterial cells. Mycolic acids have been demonstrated to have covalent linkages to arabino-galactans and thus maintain the integrity of the mycobacterial cell wall. Inhibition in their syntheses would result in a disruption of the cell wall and the death of the mycobacteria. Since mycolic acids are unique to the mycobacteria, mycolic acid biosynthetic enzymes are excellent targets for development of drugs of use in the treatment of mycobacterial infection. However, in order to develop drugs capable of inhibiting InhA activity, it is necessary to have InhA crystals from which the three dimensional structure of InhA enzyme can be determined.

It is therefore an object of this invention to provide InhA enzyme crystals.

It is another object of this invention to provide a method of determining the three dimensional structure of InhA enzyme utilizing said crystals.

It is a further object of this invention to provide the three dimensional structure of InhA enzyme.

It is a still further object of this invention to provide a method of treating mycobacterial infection utilizing compounds which block the biochemical activity of InhA enzyme.

SUMMARY OF THE INVENTION

This invention is directed to an isolated InhA enzyme comprising a first sub-structure which is a core α/βstructure composed of six parallel β strands surrounded and interwoven by four α-helices and a second sub-structure composed of two α-helices interconnected by a loop. This invention is further directed to a method of determining the three dimensional structure of the InhA enzyme by determining the structure of InhA crystals utilizing multiple isomorphous replacement, and developing a polyalanine model of the crystals, thereby obtaining the three dimensional structure of the crystals.

In addition, this invention is directed to a method of treating M. tuberculosis infection comprising the determination of the three dimensional structure of InhA enzyme from M. tuberculosis, utilization of said three dimensional structure to develop a compound which binds to said enzyme and contacting said compound with said enzyme, thereby inhibiting the biochemical activity of said enzyme and treating M. tuberculosis infection.

BRIEF DESCRIPTION OF THE DRAWING

The above brief description, as well as further objects and features of the present invention, will be more fully understood by reference to the following detailed description of the presently preferred, albeit illustrative, embodiments of the present invention when taken in conjunction with the accompanying drawing wherein.

DETAILED DESCRIPTION OF THE INVENTION

Figure 1:
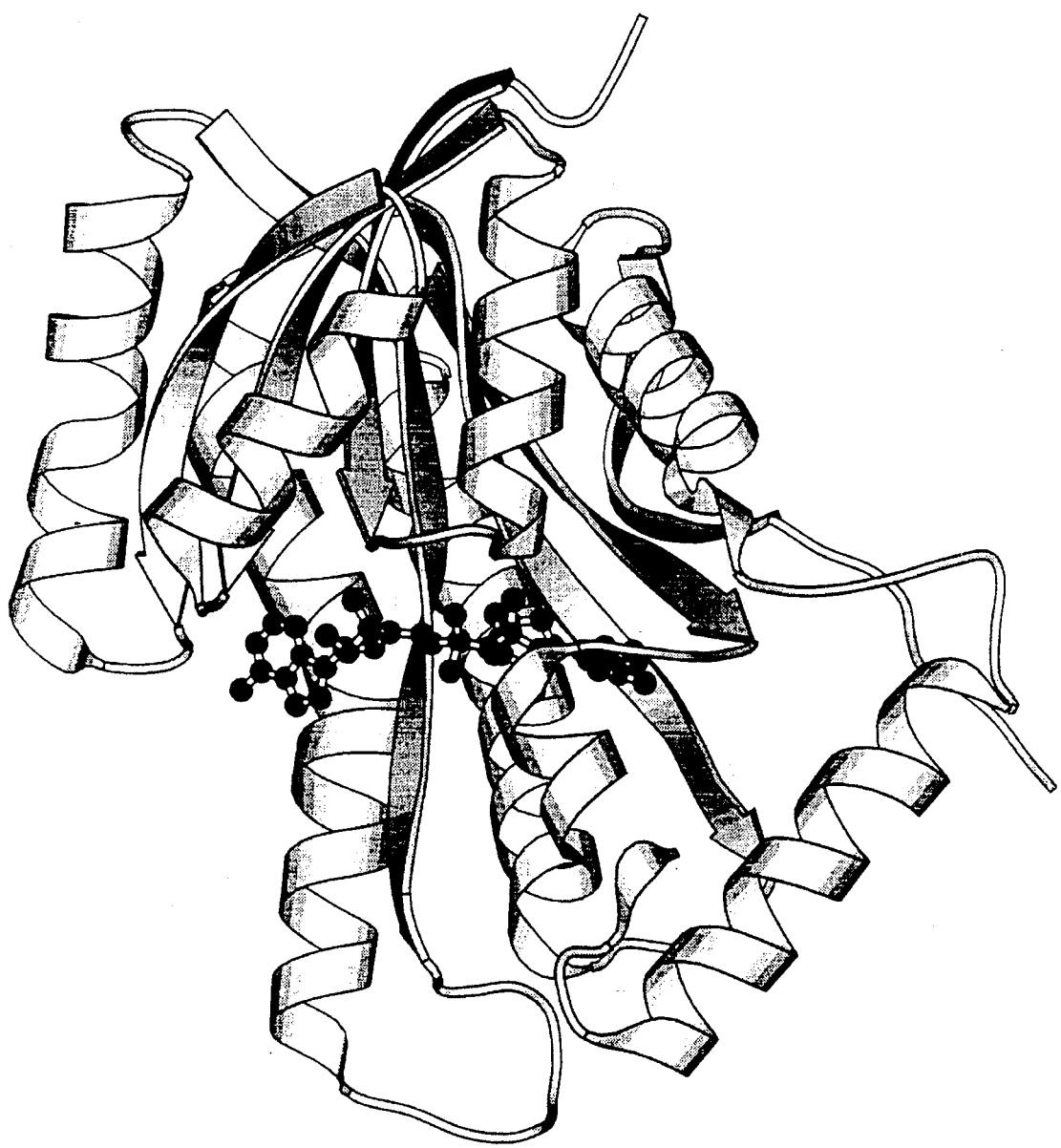
FIG. 1 represents a ribbon strand diagram of the three dimensional structure of InhA enzyme from M. tuberculosis.

InhA enzyme was overexpressed in a commercially available E. coli system and purified utilizing the nucleic acid sequence of InhA. The sequence of InhA is as follows:

| SEQ ID NO: 1 | | | | | | | |
|---|---|---|---|---|---|---|---|
| AGCGCGACAT | ACCTGCTGCG | CAATTCGTAG | GGCGTCAATA | CACCCGCAGC | CAGGGCCTCG | 60 |
| CTGCCCAGAA | AGGGATCCGT | CATGGTCGAA | GTGTGCTGAG | TCACACCGAC | AAACGTCACG | 120 |
| AGCGTAACCC | CAGTGCGAAA | GTTCCCGCCG | GAAATCGCAG | CCACGTTACG | CTCGTGGACA | 180 |
| TACCGATTTC | GGCCCGGCCG | CGGCGAGACG | ATAGGTTGTC | GGGGTGACTG | CCACAGCCAC | 240 |
| TGAAGGGGCC | AAACCCCCAT | TCGTATCCCG | TTCAGTCCTG | GTTACCGGAG | GAAACCGGGG | 300 |
| GATCGGGCTG | GCGATCGCAC | AGCGGCTGGC | TGCCGACGGC | CACAAGGTGG | CCGTCACCCA | 360 |
| CCGTGGATCC | GGAGCGCCAA | AGGGGCTGTT | TGGCGTCGAA | TGTGACGTCA | CCGACAGCGA | 420 |
| CGCCGTCGAT | CGCGCCTTCA | CGGCGGTAGA | AGAGCACCAG | GGTCCGGTCG | AGGTGCTGGT | 480 |
| GTCCAACGCC | GGCCTATCCG | CGGACGCATT | CCTCATGCGG | ATGACCGAGG | AAAAGTTCGA | 540 |
| GAAGGTCATC | AACGCCAACC | TCACCGGGGC | GTTCCGGGTG | GCTCAACGGG | CATGCGCAG | 600 |
| CATGCAGCGC | AACAAATTCG | GTCGAATGAT | ATTCATAGGT | TCGGTCTCCG | GCAGCTGGGG | 660 |
| CATCGGCAAC | CAGGCCAACT | ACGCAGCCTC | CAAGGCCGGA | GTGATTGGCA | TGGCCCGCTC | 720 |
| GATCGCCCGC | GAGCTGTCGA | AGGCAAACGT | GACCGCGAAT | GTGGTGGCCC | CGGGCTACAT | 780 |
| CGACACCGAT | ATGACCCGCG | CGCTGGATGA | GCGGATTCAG | CAGGGGGCGC | TGCAATTTAT | 840 |
| CCCAGCGAAG | CGGGTCGGCA | CCCCCGCCGA | GGTCGCCGGG | GTGGTCAGCT | TCCTGGCTTC | 900 |
| CGAGGATGCG | AGCTATATCT | CCGGTGCGGT | CATCCCGGTC | GACGGCGGCA | TGGGTATGGG | 960 |
| CCACTGACAC | AACACAAGGA | CGCACATGCAC | AGGACTGCTG | GACGGCAAAC | GGATTCTGGT | 1020 |
| TAGCGGAATC | ATCACCGACT | CGTCGATCGC | GTTTCACATC | GCACGGGTAG | CCCAGGAGCA | 1080 |
| GGGCGCCCAG | CTGGTGCTCA | CCGGGTTCGA | CCGGCTGCGG | CTGATTCAGC | GCATCACCGA | 1140 |
| CCGGCTGCCG | GCAAAGGCCC | CGCTGCTCGA | ACTCGACGTG | CAAAACGAGG | AGCACCTGGC | 1200 |
| CAGCTTGGCC | GGCCGGGTGA | CCGAGGCGAT | CGGGGCGGGC | AACAAGCTCG | ACGGGGTGGT | 1260 |
| GCATTCGATT | GGGTTCATGC | CGCAGACCGG | GATGGGCATC | AACCCGTTCT | TCGACGCGCC | 1320 |
| CTACGCGGAT | GTGTCCAAGG | GCATCCACAT | CTCGGCGTAT | TCGTATGCTT | CGATGGCCAA | 1380 |
| GGCGCTGCTG | CCGATCATGA | ACCCCGGAGG | TTCCATCGTC | GGCATGGACT | TCGACCCGAG | 1440 |
| CCGGGCGATG | CCGGCCTACA | ACTGGATGAC | GGTCGCCAAG | AGCGCGTTGG | AGTCGGTCAA | 1500 |
| CAGGTTCGTG | GCGCGCGAGG | CCGGCAAGTA | CGGTGTGCGT | TCGAATCTCG | TTGGCGCAGG | 1560 |
| CCCTATCCGG | ACGCTGGCGA | TGAGTGCGAT | CGTCGGCGGT | GCGCTCGGCG | AAGAGGCCGG | 1620 |
| CGCCCAGATC | CAGCTGCTCG | AGGAGGGCTG | GGATCAGCGC | GCTCCGATCG | GCTGGAACAT | 1680 |
| GAAGGATGCG | ACGCCGGTCG | CCAAGACGGT | GTGCGCGCTG | CTGTCTGACT | GGCTGCCGGC | 1740 |
| GACCACGGGT | GACATCATCT | ACGCCGACGG | CGGCGCCGAC | ACCCAATTGC | TCTAGAACGC | 1800 |
| ATGCAATTTG | ATGCCGTCCT | GCTGCTGTCG | TTCGGCGGAC | CGGAAGGGCC | CGAGCAGGTG | 1860 |
| CGCCCGTTCC | TGGAGAACGT | TACCCGGGGC | CGCGGTGTGC | CTGCCGAACG | GTTGGACGCG | 1920 |
| GTGGCCGAGC | ACTACCTGCA | TTTCGGTGGG | GTATCACCGA | TCAATGGCAT | TAATCGCACA | 1980 |
| CTGATCGCGG | AGCTGGAGGC | GCAGCAAGAA | CTGCCGGTGT | ACTTCGGTAA | CCGCAACTGG | 2040 |
| GAGCCGTATG | TAGAAGATGC | CGTTACGGCC | ATGCGCGACA | ACGGTGTCCG | GCGTGCAGCG | 2100 |
| GTCTTTGCGA | CATCTGCGTG | GAGCGGTTAC | TCGAGCTGCA | CACAGTACGT | GGAGGACATC | 2160 |
| GCGCGGCCCC | CCGCGCGGCC | GGGCGCGACG | CGCCTGAACT | GGTAAAACTG | CGGCCCTACT | 2220 |
| TCGACCATCC | GCTGTTCGTC | GAGATGTTCG | CCGACGCCAT | CACCGCGGCC | GCCGCAACCG | 2280 |
| TGCGCGGTGA | TGCCCGGCTG | GTGTTCACCG | CGCATTCGAT | CCCGACGGCC | GCCGACCGCC | 2340 |
| GCTGTGGCCC | CAACCTCTAC | AGCCGCCAAG | TCGCCTACGC | CACAAGGCTG | GTCGCGGCCG | 2400 |
| CTGCCGGATA | CTGCGACTTT | GACCTGGCCT | GGCAGTCGAG | ATCGGGCCCG | CCGCAGGTGC | 2460 |
| CCTGGCTGGA | GCCAGACGTT | ACCGACCAGC | TCACCGGTCT | GGCTGGGCC | GGCATCAACG | 2520 |
| CGGTGATCGT | GTGTCCCATT | GGATTCGTCG | CCGACCATAT | CGAGGTGGTG | TGGGATCTCG | 2580 |
| ACCACGAGTT | GCGATTACAA | GCCGAGGCAG | CGGGCATCGC | GTACGCCCGG | GCCAGCACCC | 2640 |
| CCAATGCCGA | CCCGCGGTTC | GCTCGACTAG | CCAGAGGTTT | GATCGACGAA | CTCCGTTACG | 2700 |
| GCCGTATACC | TGCGCGGGTG | AGTGGCCCCG | ATCCGGTGCC | GGGCTGTCTG | TCCAGCATCA | 2760 |
| ACGGCCAGCC | ATGCCGTCCG | CCGCACTGCG | TGGCTAGCGT | CAGTCCGGCC | AGGCCGAGTG | 2820 |
| CAGGATCGCC | GTGACCGCGG | ACATCCGGGC | CGAGCGCACC | ACGGCGGTCA | ACGGTCTCAA | 2880 |
| CGCATCGGTG | GCACGCTGAG | CGTCCGACAA | CGACTGCGTT | CCGATCGGCA | ATCGACTCAG | 2940 |
| CCCGGCACTG | ACCGCGATGA | TCGCATCGAC | GTGCGCGGCA | TTCTCGAGCA | CCCGCAATGC | 3000 |
| GCGCGATGGC | GCGTGGTCGG | GAACCCGGTG | TTGCCGTGAC | GATTCGAGCA | ACTGCTCGAC | 3060 |
| GAGGCCACGG | GGCTTGGCGA | CGTCGCTAGA | TCCCAGTCCG | ATGGTGCTCA | AGGCTTCGGC | 3120 |

In order to determine the three dimensional structure of InhA enzyme, recombinant InhA from *M. tuberculosis* was purified. The InhA:β-Nicotinamide adenine dinucleotide, reduced and oxidized (NADH) complex was crystallized by the hanging drop vapor diffusion method, where 3 μl of protein solution (13 mg/ml InhA, in a 1:2 ratio with NADH) were mixed with 3 μl or precipitant solution (50 mM HEPES pH 7.2, 8–12% methyl pentane diol (MPD), 50 mM sodium citrate pH 6.2) on a silanized coverslip which was inverted and sealed above 700 μl of the precipitant solution.

Single crystals of up to 0.6 mm³ in size were grown in this way at 19° C. within three weeks. The crystals were hexagonal in shape and were of the space group $P6_222$. The InhA crystals grown had unit cell dimensions of a=b=100.1 Å, c=140.4 Å, and α=β=90°, γ=120°. There was one monomer per asymmetric unit, and the solvent content of the crystals was approximately 60%. Two heavy atom derivatives (p-(chloromercury)- phenyl sulfonate (PCMPS), and $Hg(C_2H_3O_2)$) were prepared and used to determine the three dimensional structure of the crystals.

A mercury acetate derivative of the crystals was collected after a native crystal (containing NADH) was soaked overnight in 1 mM C2H302.Hg and 10% MPD, 50 mM HEPES pH 7.2, 50 mMNa-citrate pH 6.2. The PCMPS derivative was obtained by pre-reacting the protein (13 mg/ml in 10 mM HEPES, pH 7.2, with 1:2 ratio with NADH) with 10 mM PCMPS for approximately 30 minutes at 19° C. and then crystallizing the complex under the same conditions that gave native crystals. Crystals of the InhA complex were hexagonal and isomorphous with the native form and were used in multiple isomorphous replacement (MIR) procedures to determine the three dimensional structure of the InhA enzyme.

Heavy derivatives (PCMPS, mercury acetate, and lead acetate) of the $P6_222$ crystals of InhA were used to determine the three dimensional structure of InhA. The lead derivative was collected after a native crystal, originally produced in the presence of a 2:1 NADH:protein ratio, was soaked overnight in 1 mM $C_4H_6O_4$ Pb in 0.1M Na acetate, 0.1M Na HEPES, 10% MPD (methyl pentane diol), pH 6.5. The mercury derivative was collected after a native crystal grown in the same fashion was soaked overnight in 1 mM $C_4H_6O_4Hg$ in 0.1 Na citrate, 0.1M Na HEPES, 10% MPD, pH 7.2. The PCMPS derivative was obtained by mixing the protein (10 mg/mL in 10 mM HEPES, pH 7.2) with a 6-fold molar excess of PCMPS overnight at 19° C. and then crystallizing the complex under the same conditions that gave native crystals. A heavy atom derivative of InhA with PCMPS can also be obtained by utilizing the same procedure as in the lead acetate experiment, but with lower metal occupancy. Crystals of the InhA-PCMPS were hexagonal with the native form and were used in the MIR procedures.

Heavy atom binding positions were found using Patterson maps. The heavy atom binding positions (as calculated from difference Patterson maps) were refined by an iterative series of phase refinement, using the package PHASES (W. Furey, VA Medical School and University of Pittsburgh, Pa.), and XtalView (see McRee et al. (1993)), running on a Silicon Graphics. Iris computer. Solvent flattening (Wang, 1985) procedures, as implemented in PHASES, were used to further improve the MIR phases. From the resulting electron density map (up t 2.8 Å), a partial model of InhA was built.

All data sets were collected on a Siemens multiwire area detector, using a Rigaku RU-200 rotating anode X-ray source operating at 55 kV and 85 mA. Data were reduced using the Siemens package XENGEN (Siemens Analytica X-ray Instruments, Inc., Madison, Wis.) on a Silicon Graphics Iris computer. For the native data set, the R-merge on intensities was 9.6% to 2.2 Åfor 23880 reflections (81% complete). The PCMPS derivative had an R-merge on intensities of 13.9% for 26375 reflections to 2.5 Åresolution. The $HG(C_2H_3O_2)$ derivative had an R-merge on intensities of 14.3% for 26261 reflections at 2.5 Åresolution.

The three dimensional structure of InhA was determined using multiple isomorphous replacement data collected from the derivatives. Table 1, below, summarizes the statistics for phase determination.

TABLE 1

| | HEAVY ATOM DERIVATIVES OF INHA FROM MYCOBACTERIUM TUBERCULOSIS | | | | | |
|---|---|---|---|---|---|---|
| HEAVY ATOM | CONCENT | $R_{sym}$ | $R_{merge}$ | EXT. Diffr. (Å) | N° SITES | PHASING POWER |
| $Hg(C_2H_3O_2)_2$ | 1 mM | 0.143 | 0.106 | 2.5 | 1 | 1.55 |
| PCMPS CO-CRYSTAL | 2 mM | 0.139 | 0.107 | 2.5 | 4 | 1.60 |

Data produced a mean figure of merit of 0.499 for 11061 phased reflections with F >1δ. Solvent flattening (Wang, 1985) procedures, as implemented in PHASES, were used to further improve the MIR phases. From the resulting electron density map, a partial polyalanine model was built using the program TOM, a derivative of FRODO (Jones, 1985), displayed on an Iris Graphics workstation.

The polyalanine model was refined using molecular dynamics and energy minimization (see Brunger et al. (1987)). In the first step, the simulated annealing procedure "slow cool" (see Brunger (1992)) was used. Electron density maps (both $2|F_o-F_c|$ and $|F_o-F_c|$) were using the atomic coordinates of the polyalanine model. Subsequently, the use of a combination of the MIR map and combined maps (maps obtained combining model-based and MIR phases) allowed for the tracing of the complete model and the incorporation of the complete amino acid sequence, as well as the bound NADH moiety.

It was determined by the inventors that recombinant InhA from *M. tuberculosis* is a single-domain enzyme, shown as a ribbon strands diagram in FIG. 1. Two substructures can be identified in the protein. The first substructure is a core α/β structure composed of six parallel β strands surrounded and interwoven by four α-helices, harboring the N-terminal section of the macromolecule. The second substructure is a C-terminal region, composed mainly of two α-helices interconnected by a short loop. The topology of substructure 1 emulates that of the dinucleotide binding fold of many dehydrogenases in that it contains a twisted β-sheet in the middle, surrounded by α-helices.

This substructure can be divided into two sections. The first section consists of two β strands (B-1 and B-2) and two short α-helices (A-1 and A-2). This section is connected to the second section of the fold by a third β strand (B-3), which crosses over to the other side of the structure. The second part of the fold consists of an α-helix (A-3), connected by a long loop to the 4th 14-residue β strand (B-4). A fourth α-helix (A-4) connects into a fifth β strand (B-5), which is followed by a 25-residue α-helix (A-5). This structure then connects into a sixth β strand (B-6), which is the last secondary structural motif in the nucleotide binding fold. The second part of the nucleotide-binding fold is unusual in that the helices are of very long nature. The longest α-helix, A-5, may be interacting with the carboxyl terminal helices.

A short loop connects the nucleotide binding fold to the carboxyl terminal domain, which consists of a short β strand (B-7) followed by two helices (A-6 and A-7) interconnected by a 5-residue loop. The C-terminal portion of the molecule consists of two other α-helical structures.

The active site of InhA lies on a cavity on the surface of the molecule, formed by the carboxyl termini of the β sheets which participate in the α/β core and two α-helices, A-5 and A-6. NADH lies in an extended conformation along the top of the carboxyl termini of the core sheet, in a binding manner which is commonly observed in dinucleotide binding enzymes. The substrate binding site is in the hydrophobic cavity composed of helices 4, 5 and 6, which are highly rich in hydrophobic residues. The hydrophobic nature of this cavity likely renders it optimal for the accommodation of the lipid substrate in close proximity to the nicotinamide moiety of NADH. It is also likely that the three aforementioned helices form a core which acts as a flexible diaphragm which expands upon substrate binding.

The three dimensional structure of InhA enzyme can be utilized to develop compounds which bind to InhA enzyme thereby inhibiting the biochemical activity of InhA enzyme, such as mycolic acid biosynthesis. Specifically, compounds can be designed which bind to the active site and/or the NADH region on the InhA enzyme to inhibit the biochemical activity of the InhA enzyme. Hence, the compounds which are developed utilizing the three dimensional structure of InhA enzyme can be administered to treat *M. tuberculosis* infection.

Although the invention herein has been described with reference to particular embodiments, it is to be understood that these embodiments are merely illustrative of various aspects of the invention. Thus, it is to be understood that numerous modifications may be made in the illustrative embodiments and other arrangements may be devised without departing from the spirit and scope of the invention.

We claim:

1. An isolated Inha enzyme-NADH crystallized complex in the form of a hexagon with a space group $P6_222$, and having unit cell constants of a=b=100.1 Å, c=140.4 Å, and $\alpha=\beta=90°$, $\gamma=120°$.

* * * * *

SEQUENCE LISTING ( 1 ) GENERAL INFORMATION:

( i i i ) NUMBER OF SEQUENCES: 1

( 2 ) INFORMATION FOR SEQ ID NO: 1:

( i ) SEQUENCE CHARACTERISTICS:
( A ) LENGTH: 3120
( B ) TYPE: nucleic acid
( C ) STRANDEDNESS: single
( D ) TOPOLOGY: both ( i i ) MOLECULE TYPE: DNA
( A ) DESCRIPTION:

( i i i ) HYPOTHETICAL: No ( i v ) ANTI-SENSE:

( v ) FRAGMENT TYPE:

( v i ) ORIGINAL SOURCE: inhA operon
( A ) ORGANISM: M tuberculosis
( B ) STRAIN:
( C ) INDIVIDUAL ISOLATE:
( D ) DEVELOPMENTAL STAGE:
( E ) HAPLOTYPE:
( F ) TISSUE TYPE:
( G ) CELL TYPE:
( H ) CELL LINE:
( I ) ORGANELLE:

( v i i ) IMMEDIATE SOURCE: M tuberculosis ( v i i i ) POSITION IN GENOME:
( A ) CHROMOSOME/SEGMENT:
( B ) MAP POSITION:
( C ) UNITS:

( i x ) FEATURE:
( A ) NAME/KEY:
( B ) LOCATION:
( C ) IDENTIFICATION METHOD:
( D ) OTHER INFORMATION:

( x ) PUBLICATION INFORMATION: None
    ( A ) AUTHORS:
    ( B ) TITLE:
    ( C ) JOURNAL:
    ( D ) VOLUME:
    ( F ) PAGES:
    ( G ) DATE:
    ( H ) DOCUMENT NUMBER:
    ( I ) FILING DATE:
    ( J ) PUBLICATION DATE:
    ( K ) RELEVANT RESIDUES IN SEQ ID NO:

( x i ) SEQUENCE DESCRIPTION: SEQ ID NO: 1:

```
AGCGCGACAT  ACCTGCTGCG  CAATTCGTAG  GGCGTCAATA  CACCCGCAGC  CAGGGCCTCG     60
CTGCCCAGAA  AGGGATCCGT  CATGGTCGAA  GTGTGCTGAG  TCACACCGAC  AAACGTCACG    120
AGCGTAACCC  CAGTGCGAAA  GTTCCCGCCG  GAAATCGCAG  CCACGTTACG  CTCGTGGACA    180
TACCGATTTC  GGCCCGGCCG  CGGCGAGACG  ATAGGTTGTC  GGGGTGACTG  CCACAGCCAC    240
TGAAGGGGCC  AAACCCCCAT  TCGTATCCCG  TTCAGTCCTG  GTTACCGGAG  GAAACCGGGG    300
GATCGGGCTG  GCGATCGCAC  AGCGGCTGGC  TGCCGACGGC  CACAAGGTGG  CCGTCACCCA    360
CCGTGGATCC  GGAGCGCCAA  AGGGGCTGTT  TGGCGTCGAA  TGTGACGTCA  CCGACAGCGA    420
CGCCGTCGAT  CGCGCCTTCA  CGGCGGTAGA  AGAGCACCAG  GGTCCGGTCG  AGGTGCTGGT    480
GTCCAACGCC  GGCCTATCCG  CGGACGCATT  CCTCATGCGG  ATGACCGAGG  AAAAGTTCGA    540
GAAGGTCATC  AACGCCAACC  TCACCGGGGC  GTTCCGGGTG  GCTCAACGGG  CATCGCGCAG    600
CATGCAGCGC  AACAAATTCG  GTCGAATGAT  ATTCATAGGT  TCGGTCTCCG  GCAGCTGGGG    660
CATCGGCAAC  CAGGCCAACT  ACGCAGCCTC  CAAGGCCGGA  GTGATTGGCA  TGGCCCGCTC    720
GATCGCCCGC  GAGCTGTCGA  AGGCAAACGT  GACCGCGAAT  GTGGTGGCCC  CGGGCTACAT    780
CGACACCGAT  ATGACCCGCG  CGCTGGATGA  GCGGATTCAG  CAGGGGGCGC  TGCAATTTAT    840
CCCAGCGAAG  CGGGTCGGCA  CCCCCGCCGA  GGTCGCCGGG  GTGGTCAGCT  TCCTGGCTTC    900
CGAGGATGCG  AGCTATATCT  CCGGTGCGGT  CATCCCGGTC  GACGGCGGCA  TGGGTATGGG    960
CCACTGACAC  AACACAAGGA  CGCACATGAC  AGGACTGCTG  GACGGCAAAC  GGATTCTGGT   1020
TAGCGGAATC  ATCACCGACT  CGTCGATCGC  GTTTCACATC  GCACGGGTAG  CCCAGGAGCA   1080
GGGCGCCCAG  CTGGTGCTCA  CCGGGTTCGA  CCGGCTGCGG  CTGATTCAGC  GCATCACCGA   1140
CCGGCTGCCG  GCAAAGGCCC  CGCTGCTCGA  ACTCGACGTG  CAAAACGAGG  AGCACCTGGC   1200
CAGCTTGGCC  GGCCGGGTGA  CCGAGGCGAT  CGGGCGGGC   AACAAGCTCG  ACGGGGTGGT   1260
GCATTCGATT  GGGTTCATGC  CGCAGACCGG  GATGGGCATC  AACCCGTTCT  TCGACGCGCC   1320
CTACGCGGAT  GTGTCCAAGG  GCATCCACAT  CTCGGCGTAT  TCGTATGCTT  CGATGGCCAA   1380
GGCGCTGCTG  CCGATCATGA  ACCCCGGAGG  TTCCATCGTC  GGCATGGACT  TCGACCCGAG   1440
CCGGGCGATG  CCGGCCTACA  ACTGGATGAC  GGTCGCCAAG  AGCGCGTTGG  AGTCGGTCAA   1500
CAGGTTCGTG  GCGCGCGAGG  CCGGCAAGTA  CGGTGTGCGT  TCGAATCTCG  TTGGCGCAGG   1560
CCCTATCCGG  ACGCTGGCGA  TGAGTGCGAT  CGTCGGCGGT  GCGCTCGGCG  AAGAGGCCGG   1620
CGCCCAGATC  CAGCTGCTCG  AGGAGGGCTG  GGATCAGCGC  GCTCCGATCG  GCTGGAACAT   1680
GAAGGATGCG  ACGCCGGTCG  CCAAGACGGT  GTGCGCGCTG  CTGTCTGACT  GGCTGCCGGC   1740
GACCACGGGT  GACATCATCT  ACGCCGACGG  CGGCGCGCAC  ACCCAATTGC  TCTAGAACGC   1800
ATGCAATTTG  ATGCCGTCCT  GCTGCTGTCG  TTCGGCGGAC  CGGAAGGGCC  CGAGCAGGTG   1860
CGCCCGTTCC  TGGAGAACGT  TACCCGGGGC  CGCGGTGTGC  CTGCCGAACG  GTTGGACGCG   1920
GTGGCCGAGC  ACTACCTGCA  TTTCGGTGGG  GTATCACCGA  TCAATGGCAT  TAATCGCACA   1980
```

| | | | | | |
|---|---|---|---|---|---|
| CTGATCGCGG | AGCTGGAGGC | GCAGCAAGAA | CTGCCGGTGT | ACTTCGGTAA | CCGCAACTGG | 2040 |
| GAGCCGTATG | TAGAAGATGC | CGTTACGGCC | ATGCGCGACA | ACGGTGTCCG | GCGTGCAGCG | 2100 |
| GTCTTTGCGA | CATCTGCGTG | GAGCGGTTAC | TCGAGCTGCA | CACAGTACGT | GGAGGACATC | 2160 |
| GCGCGGCCCC | CCGCGCGGCC | GGGCGCGACG | CGCCTGAACT | GGTAAAACTG | CGGCCCTACT | 2220 |
| TCGACCATCC | GCTGTTCGTC | GAGATGTTCG | CCGACGCCAT | CACCGCGGCC | GCCGCAACCG | 2280 |
| TGCGCGGTGA | TGCCCGGCTG | GTGTTCACCG | CGCATTCGAT | CCCGACGGCC | GCCGACCGCC | 2340 |
| GCTGTGGCCC | CAACCTCTAC | AGCCGCCAAG | TCGCCTACGC | CACAAGGCTG | GTCGCGGCCG | 2400 |
| CTGCCGGATA | CTGCGACTTT | GACCTGGCCT | GGCAGTCGAG | ATCGGGCCCG | CCGCAGGTGC | 2460 |
| CCTGGCTGGA | GCCAGACGTT | ACCGACCAGC | TCACCGGTCT | GGCTGGGGCC | GGCATCAACG | 2520 |
| CGGTGATCGT | GTGTCCCATT | GGATTCGTCG | CCGACCATAT | CGAGGTGGTG | TGGGATCTCG | 2580 |
| ACCACGAGTT | GCGATTACAA | GCCGAGGCAG | CGGGCATCGC | GTACGCCCGG | GCCAGCACCC | 2640 |
| CCAATGCCGA | CCCGCGGTTC | GCTCGACTAG | CCAGAGGTTT | GATCGACGAA | CTCCGTTACG | 2700 |
| GCCGTATACC | TGCGCGGGTG | AGTGGCCCCG | ATCCGGTGCC | GGGCTGTCTG | TCCAGCATCA | 2760 |
| ACGGCCAGCC | ATGCCGTCCG | CCGCACTGCG | TGGCTAGCGT | CAGTCCGGCC | AGGCCGAGTG | 2820 |
| CAGGATCGCC | GTGACCGCGG | ACATCCGGGC | CGAGCGCACC | ACGGCGGTCA | ACGGTCTCAA | 2880 |
| CGCATCGGTG | GCACGCTGAG | CGTCCGACAA | CGACTGCGTT | CCGATCGGCA | ATCGACTCAG | 2940 |
| CCCGGCACTG | ACCGCGATGA | TCGCATCGAC | GTGCGCGGCA | TTCTCGAGCA | CCCGCAATGC | 3000 |
| GCGCGATGGC | GCGTGGTCGG | GAACCCGGTG | TTGCCGTGAC | GATTCGAGCA | ACTGCTCGAC | 3060 |
| GAGGCCACGG | GGCTTGGCGA | CGTCGCTAGA | TCCCAGTCCG | ATGGTGCTCA | AGGCTTCGGC | 3120 |